United States Patent
He et al.

(10) Patent No.: US 6,956,928 B2
(45) Date of Patent: Oct. 18, 2005

(54) VERTICAL SMALL ANGLE X-RAY SCATTERING SYSTEM

(75) Inventors: Bob Baoping He, Madison, WI (US); Rolf Dieter Schipper, Karlsruhe (DE)

(73) Assignee: Bruker AXS, Inc., Madison, WI (US)

( * ) Notice: Subject to any disclaimer, the term of this patent is extended or adjusted under 35 U.S.C. 154(b) by 119 days.

(21) Appl. No.: 10/429,926

(22) Filed: May 5, 2003

(65) Prior Publication Data

US 2004/0223586 A1 Nov. 11, 2004

(51) Int. Cl.$^7$ .............................................. G01N 23/201
(52) U.S. Cl. ............................ 378/87; 378/70; 378/71; 378/80; 378/86; 378/89
(58) Field of Search .............................. 378/43, 44–47, 378/49, 70–73, 79, 80, 86–90, 208

(56) References Cited

U.S. PATENT DOCUMENTS

| | | |
|---|---|---|
| 4,751,722 A | 6/1988 | Harding et al. |
| 4,956,856 A | 9/1990 | Harding |

(Continued)

FOREIGN PATENT DOCUMENTS

| | | |
|---|---|---|
| EP | 04010240.2 | 10/2004 |

OTHER PUBLICATIONS

B. D. Cullity. Elements of X–Ray Diffraction, second edition (Reading, MA: Addison–Wesley, 1978), p. 285.*

Norma F. Carnahan et al., A Small Angle X–ray Scattering Study of the Effect of Pressure on the Aggregation of Asphaltene Fractions in Petroleum Fluids under Near–Critical Solvent Conditions; Langmuir 1993, 9, pp. 2035–2044.

Hisashi Hayashi et al., Construction of a Small–angle X–Ray Scattering Diffractometer for the Study of Fluctuations in Solutions; 362 Japanese Journal of Applied Physics 28 Aug. (1989), No. 8, Part 1, Tokyo, JP; pp. 1501–1503.

(Continued)

*Primary Examiner*—Allen C. Ho
(74) *Attorney, Agent, or Firm*—Kudirka & Jobse, LLP

(57) ABSTRACT

A small angle x-ray diffraction scattering system has a vertical orientation, allowing for simplified analysis of liquid samples. The system may function in a beam-up or a beam-down configuration. An x-ray source provides an initial x-ray beam that is directed vertically along a primary beampath to a sample located on a sample support. The small angle scattered x-ray energy travels through a secondary beampath to a detector. The primary and secondary beampaths may be evacuated and separated from a sample chamber by fluid seals. Beam conditioning optics and a collimator may be used in the primary beampath, and a beamstop used in the secondary beampath. The sample chamber may have a microscope or camera, which may be movable, for observing the sample, and a translation stage for moving the sample in at least two dimensions.

35 Claims, 3 Drawing Sheets

U.S. PATENT DOCUMENTS

| | | | | |
|---|---|---|---|---|
| 5,351,279 | A | * | 9/1994 | She et al. ..................... 378/43 |
| 5,528,646 | A | * | 6/1996 | Iketaki et al. ................. 378/43 |
| 5,589,690 | A | * | 12/1996 | Siewert et al. ......... 250/390.06 |
| 5,982,847 | A | * | 11/1999 | Nelson ........................ 378/47 |
| 6,118,850 | A | * | 9/2000 | Mayo et al. .................. 378/83 |
| 6,163,592 | A | * | 12/2000 | He et al. ..................... 378/71 |
| 6,175,117 | B1 | * | 1/2001 | Komardin et al. ..... 250/363.06 |
| 6,330,301 | B1 | * | 12/2001 | Jiang .......................... 378/85 |
| 6,442,233 | B1 | * | 8/2002 | Grodzins et al. ............. 378/57 |
| 6,483,891 | B1 | * | 11/2002 | Lazarev et al. ............... 378/37 |
| 6,653,628 | B2 | * | 11/2003 | Lee et al. .................. 250/305 |
| 6,751,288 | B1 | * | 6/2004 | Hessler ........................ 378/86 |
| 2004/0008815 | A1 | * | 1/2004 | Hoshino et al. ............. 378/86 |
| 2004/0206908 | A1 | * | 10/2004 | Lange et al. ................ 250/393 |

OTHER PUBLICATIONS

Melvyn Foklard et al., Two Approaches For Irradiating Cells Individually: A Charged–Particle Microbeam And A Soft X–Ray Microprobe; Nuclear Instruments and Methods in Physics Reasearch B 130 (1997) pp. 270–274; 1997 Elsevire Science B. V..

D. Lozano–Castello et al.; Characterization of pore distribution in activated carbon fibers by microbeam small angle X–ray scattering; Piergamon; Carbon 40 (2002) pp. 2727–2735; Elsevier Science Ltd..

H. F. Gleeson, et al.; Apparatus for simultaneous observation of the electro–optic response and small angle x–ray scattering in liquid crystals; 8127 Review of Scientific Instruments 66 Jun. (1995), No. 6, pp. 3563–3568; Woodbury, NY, US; 1995 American Institute of Physics.

J. Kral, et al.; PIXE setup for liquid sample analysis; Nuclear Instruments and Methods in Physics Research Section B: Beam Interactions with Materials and Atoms, North–Holland Publishing Company. Amsterdam, NL, vol. 109/110 1 Apr. 1996) pp. 167–169; II. Experimental; 1996 Elsevier Science B.V..

Matija Tomšič et al. Small–Angle X–Ray Scattering Study of Polyelectrolyte Solutions; Acta Chimica Slovenika vol. 48, No. 3, Jul. 2001; pp. 333–342.

* cited by examiner

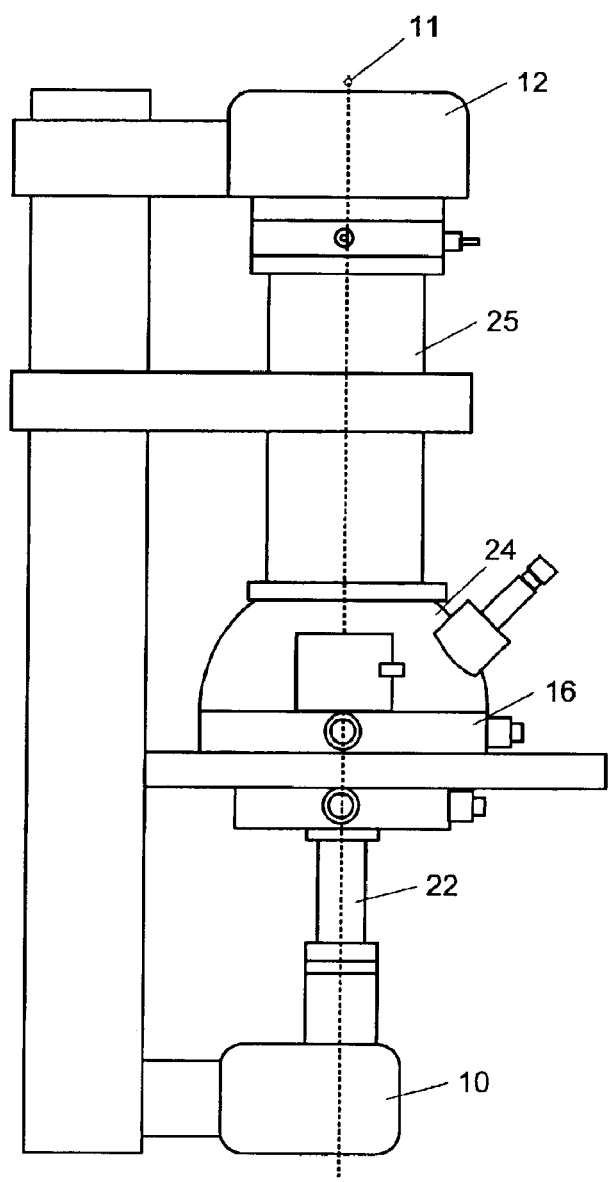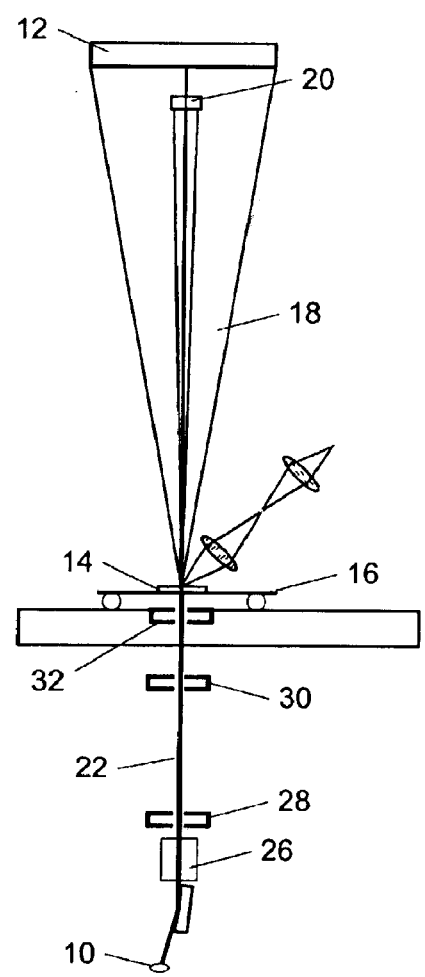
FIGURE 1A  FIGURE 1B

VERTICAL SMALL ANGLE X-RAY SCATTERING SYSTEM

FIELD OF THE INVENTION

This invention relates generally to the field of x-ray scattering analysis and, more specifically, to small angle x-ray scattering analysis systems.

BACKGROUND OF THE INVENTION

Small angle x-ray scattering is a specialized area within the more general field of x-ray scattering analysis. Unlike the more general wide-angle scattering systems, small angle systems measure phenomena that are observed within angles of just a few degrees from the primary x-ray beam. Thus, such systems may be used to provide structural information on the order of approximately one to one hundred nanometers. This allows characterization of a variety of materials that are not measurable using a wide angle system. However, small angle systems must also face a number of additional problems due to the small angle measurements.

In a small angle x-ray scattering system, the distance between the sample being examined and the x-ray detector is typically much longer than that of a wide angle system. Because of the small angular deviation from the main x-ray beam, it is necessary to have this additional length to allow adequate resolution at the x-ray detector. This, of course, increases the noise factor of the system, as the scattered x-rays have an increased opportunity to interact with ambient gas molecules. For this reason, small angle systems typically use an evacuated beampath between the sample and the detector to reduce the ambient gas density. In addition, such systems often make use of x-ray collimating apparatus located between the x-ray source and the sample. The collimator helps to reduce the incidence of parasitic capacitance, and the primary beampath within which the collimator is located may also be evacuated to reduce the presence of ambient gas molecules.

SUMMARY OF THE INVENTION

In accordance with the present invention, a small angle x-ray scattering system is provided that is oriented in a vertical configuration. This configuration is in contrast to the prior art horizontal systems. Although the horizontal systems make it relatively simple to access system components, they suffer from several drawbacks. One of these is in the area of liquid samples. When a liquid sample is examined in a horizontal small angle scattering system, it is necessary to contain the liquid in some form of vertical container, such as a capillary. However, when stored in such capillaries, the liquid samples are typically not homogeneous in thickness in directions parallel to the x-ray beam direction. Moreover, a significant amount of container surface area is encountered by the source x-ray beam, resulting in additional unwanted scattering signals, and the samples are relatively difficult to load and manipulate within the system.

In the present invention, the x-ray beam of the small angle x-ray scattering apparatus travels along a vertical path. The vertical beam may be in either an upward or a downward direction. The beam is provided by an x-ray source that outputs the beam in the vertical direction toward a sample support. The sample support maintains the sample in a position that intersects the x-ray beam such that the x-ray energy is scattered from the sample along angles close to the vertical direction. The scattered x-ray energy is then detected by an x-ray detector that is positioned to detect x-ray energy that is scattered along directions of less than five degrees relative to the vertical direction.

The front portion of the system, including the x-ray source, may be located in a primary beampath that is isolated from an external environment. This primary beampath leads to a sample chamber in which the sample support is located. The sample chamber may itself be isolated from the external environment, and may be provided with at least one access port that provides access to the sample from the outside. In addition, the primary beampath may be evacuated, and the primary beampath and sample chamber separated by a diaphragm that creates a fluid seal to maintain the vacuum. The back end of the system, including the detector, may be located in a secondary beampath that is also isolated from the external environment. As with the primary beampath, the secondary beampath may be evacuated, and may be separated from the sample chamber by a diaphragm. The secondary beampath may also extend into the sample chamber to minimize the distance that the scattered x-ray energy must travel through the unevacuated space of the sample chamber.

Other components may also be used with the system. X-ray optics 26, which condition the x-rays into desired spectrum and distribution profiles, are typically used in the primary beampath. A collimator, such as a pinhole collimator, may also be used to collimate the x-ray beam from the x-ray source before it reaches the sample. A translation stage that is movable in at least two perpendicular directions may be attached to the sample support to allow positioning of the sample, and the translation stage may be motorized. A microscope may also be used that is positioned to view the sample. The microscope may be an optical microscope or may make use of a video camera. Such a video camera system can be used, for example, with a motorized translation stage to allow automatic positioning of the sample. A video camera may also be movable, possibly by a motor, between a position in which it has a good view of the sample, but obstructs a path between the sample and detector, and a position in which there is not such obstruction. In this way, the camera may be moved to a good viewing position during positioning of the sample, and then moved out of the way during x-ray scattering. A beamstop may also be located in the system between the sample and the detector, and may be positioned to attenuate a portion of the x-ray beam that passes through the sample without being scattered.

BRIEF DESCRIPTION OF THE DRAWINGS

The above and further advantages of the invention may be better understood by referring to the following description in conjunction with the accompanying drawings in which:

FIG. 1A is a schematic front view of a small angle scattering system according to the present invention;

FIG. 1B is a schematic front view of some of the internal components of the system of FIG. 1A;

DETAILED DESCRIPTION

Figure 2:
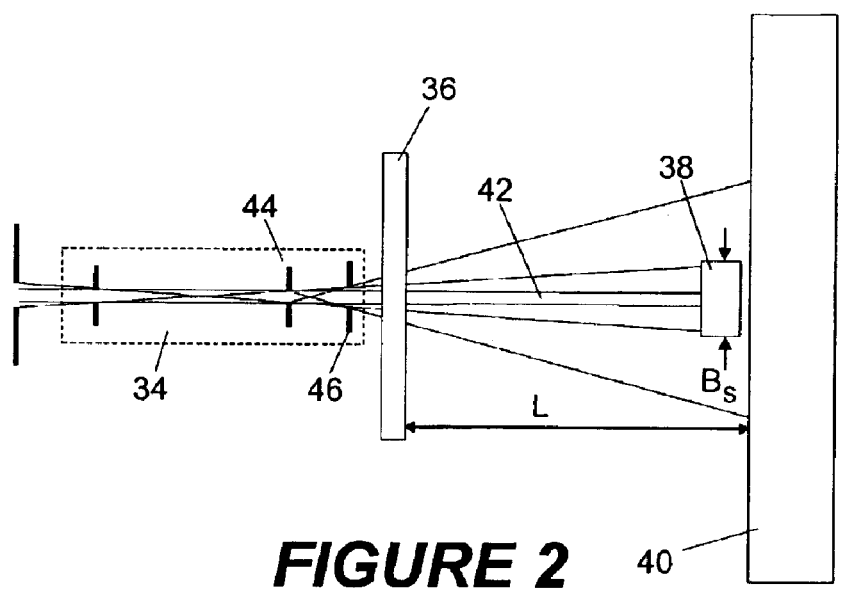
FIG. 2 is a schematic diagram showing the operation of a pinhole collimator in the system of FIGS. 1A and 1B.

Shown in FIG. 1A is a front view of a small angle x-ray scattering analysis system according to the present invention. FIG. 1B shows a more schematic arrangement of the interior components of this system for sake of clarity. The same reference numerals are used, respectively, in each of the two figures to indicate common components and thereby allow correspondence between them. As shown, the system is oriented with the x-ray transmission axis 11 in a vertical orientation with an x-ray source 10 located at the bottom and an x-ray detector 12 at the top. Those skilled in the art will recognize that an alternative configuration could also be used in which the x-ray source 10 was located at the top and the detector at the bottom, while still maintaining the system in a vertical configuration.

The source 10 is a conventional x-ray source for use with small-angle scattering systems, such as a sealed x-ray tube or a rotating anode generator, with spot focus being preferred. As an example, a copper anode source may be used that has an output wavelength $K_\alpha=1.541838$ Å. In a sealed tube or rotating anode generator, x-rays are produced by the bombardment of the target anode with electrons generated from a filament (cathode). The area bombarded by the electrons is called the focal spot on the target, and its size and shape determines the projection of the x-rays from the target. The x-rays are projected at a takeoff angle from the anode surface and form what is referred to as the spot focus.

X-rays generated from a sealed x-ray tube or rotating anode generator consist of white radiation with characteristic radiation wavelengths. Typically, only one specific characteristic line, usually $K_\alpha$, is needed. Therefore, since the white radiation produces a high noise background, and unwanted characteristic lines produce extra scattering features scrambled with a desired scattering pattern, these other wavelengths may be eliminated. In the present embodiment, x-ray optics 26 may be provided for this purpose. These optics condition the x-rays into desired spectrum and distribution profiles, and may include a crystal monochromator, capillaries, x-ray filters or an x-ray mirror or mirror group. In the present example, a graded multilayer x-ray mirror (also known as a Gobel Mirror) is used. Such mirrors are known in the art. A crossed-coupled arrangement of these optics would provide a highly parallel beam that is significantly more intense than can be obtained with the combination of pinhole collimation and a graphite monochromator. As used in the embodiment shown in FIGS. 1A and 1B, the multilayer mirrors are located at 26. For small angle applications requiring strong collimation of the beam, Gobel Mirrors would provide high intensity, due to the relatively small beam size.

The alternative embodiment of a monochromator may also be used to allow only a selected characteristic line to pass through the primary beampath. Those skilled in the art will recognize that, in practice, the reflected beam from a monochromator is not strictly monochromatic because of the mosaic of the crystal. However, the desired reduction of x-ray energy in other wavelengths is largely accomplished. In one version of this example, a flat graphite crystal monochromator is used.

The output of the x-ray source is directed toward a sample 14 located on the sample support of an XY translation stage 16. The XY translation stage allows the position of the sample to be adjusted in the two dimensions perpendicular to the beam axis. An XYZ translation stage may also be used to allow translation in both the XY directions and the Z direction (parallel to the beam axis) as well. The x-ray beam undergoes scattering from the sample, the scattered energy being indicated at 18. Positioned to receive and detect the scattered x-ray energy is two-dimensional x-ray detector 12, which detects the x-ray energy according to its intensity and position in a two-dimensional plane perpendicular to the beam axis. The portion of the beam that passes through the sample without scattering is blocked or attenuated by beamstop 20.

Because the scattering system is in a vertical configuration, the sample 14 resides in a horizontal plane. This provides several distinct advantages. First, the sample may be placed on a thin sample support, such as a piece of polyester film. If the sample is a liquid, it will spread naturally under the force of gravity, providing a relatively homogeneous thickness across the width of the sample. In addition, because the sample does not need to be contained, such as is the case with a vertically mounted sample, which must be held in a capillary or other similar container, there can be only one additional layer of material through which the source x-ray beam must pass. That is, whereas a sample contained in a capillary requires that the x-ray beam pass through two glass layers, only one layer (beneath the sample) is encountered by the beam in the present invention. Thus, there is significantly less noise due to scattering by the sample support. This allows liquid samples to be handled more easily and with less noise than in a conventional horizontal system. Because of the horizontal orientation of the sample in the present embodiment, sample changing is also significantly easier, since the sample support may simply rest on the translation stage 16, rather than requiring a holding mechanism.

As shown in FIGS. 1A and 1B, the present embodiment may be viewed as three sections: the primary beampath 22; the sample chamber 24; and the secondary beampath 25. Although such segmentation is not necessary to the invention, it will be discussed as such herein to aid in description. A first section is the primary beampath. The primary beampath receives the x-ray energy from the source 10 and couples it to an adjacent sample chamber 24. Some form of collimating means are provided along the primary beampath 22. In the embodiment of FIGS. 1A and 1B, a series of pinholes are used, as shown in the schematic drawing of FIG. 1B. First, however, the beam passes through x-ray optics 26, which condition the x-rays into desired spectrum and distribution profiles. As discussed above, these optics may include components such as a crystal monochromator, capillaries, x-ray filters or an x-ray mirror or mirror group. Such optics are known in the art, and are therefore not discussed herein in any further detail.

In order to minimize scattering by ambient air molecules, the primary beampath 22 may be evacuated. A vacuum port, not shown in the figures, may be provided for this purpose. After exiting the x-ray optics 26, the x-ray beam encounters the first pinhole 28 in the series of pinholes used in the primary beampath 22. The position of each of the pinholes 28, 30, 32 may be adjusted independently in a direction perpendicular to the x-ray beam to achieve optimal collimation and to remove parasitic scattering. FIG. 2 depicts the operation of a pinhole collimator as used with the present invention. The resolution of the system depends on the resolution of the detector, the distance between the sample and detector, and X-ray beam collimation. The collimation system defines the size, shape and divergence of the x-ray beam. When a two-dimensional detector is used, pinholes may be used to collimate the X-ray beam. The example shown in FIG. 2 shows the collimation of the system with pinhole collimator 34, sample 36, beamstop 38 and detector 40. The beam 42 that passes undiffracted through the sample, consisting of parallel and divergent components, is attenuated by the beamstop 38, and thereby prevented from significantly impacting on the detection surface. For this configuration, the maximum angular resolution $\alpha_{max}$ is given as $$\alpha_{max} = \alpha_1 + \alpha_2$$

where $\alpha_1$ is the maximum angular divergence of the incident beam, and $\alpha_2$ is the maximum angular deviation of the x-rays recorded in the detector, defined by the size of the beam spot (D) on the sample and the size of the spatial resolution element (d) of the detector, for example, d=0.2 mm for a given detector. $\alpha_2$ may then be found as $$\alpha_2 = \frac{D+d}{L}$$

where L is the separation between the sample 36 and the detector in the direction of the beam travel. The resolution R, defined as the theoretically largest Bragg spacing, is then given by $$R = \lambda / \alpha_{max}$$

where $\lambda$ is the wavelength of the x-ray radiation. R is chosen so that for a lattice spacing smaller than R, the angle between two consecutive orders of Bragg-reflections is larger than $\alpha_{max}$. The actual achievable resolution is also limited by the beamstop size $B_s$, and the resolution limit of the beamstop, $R_{BS}$, is given as $$R_{BS} = \lambda \cdot \frac{2L}{B_s}$$

The pinhole scattering is defined as the scattering from the pinhole materials, that is, after the $2^{nd}$ pinhole 44 shown in FIG. 2. The region of the pinhole scattering, however, is limited by an anti-scattering pinhole 46, which is the $3^{rd}$ pinhole shown in FIG. 2. The size of the anti-scattering pinhole should be small enough to block as much pinhole scattering as possible, but not so small as to "touch" the primary beam. The pinhole scattering, observed as a halo around the shadow of the beamstop, is also called as parasitic scattering. If the scattering signal from the sample is much stronger than the parasitic scattering, or if the halo is evenly distributed around the beamstop, the parasitic scattering will not limit the achievable resolution. Some efforts are necessary to reduce the parasitic scattering, such as ensuring a highly parallel beam (for example, by using Göbel cross-coupled mirrors), or using a smaller pinhole size and appropriate pinhole combination.

Figure 3:
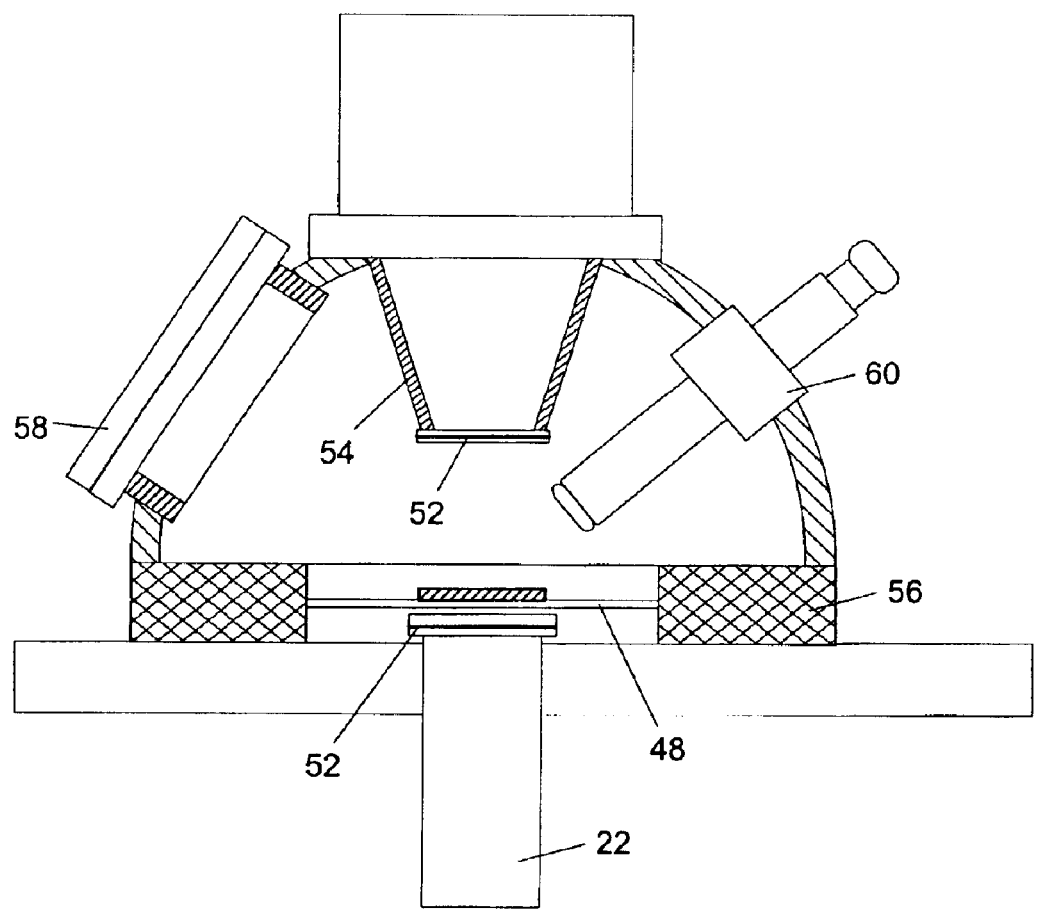
FIG. 3 is a schematic view of the interior of a sample chamber of the system shown in FIGS. 1A and 1B.

After passing through the pinhole collimator, the primary x-ray beam enters the sample chamber 24. A schematic view of the sample chamber is shown in FIG. 3. In order to maximize the transmission efficiency of the x-ray beam, the primary beampath may be either under a vacuum or filled with a low density gas, such as helium. The sample chamber may also be an enclosed space so as to control the environment of the sample. Similarly, the secondary beampath may also be under vacuum or filled with a low-density gas to minimize air scattering. Therefore, the sample chamber may be separated from the primary and secondary beampaths by diaphragms 52 that maintain an airtight separation between them. Such diaphragms may be materials with low x-ray absorption, such as beryllium or Kapton foil. In this way, the sample chamber may be under an environment different from the primary and secondary beampaths. In addition, in the embodiment shown, a portion 54 of the secondary beampath extends into the sample chamber so as to reduce the distance that the scattered x-rays must travel in the sample chamber environment. Although vacuum ports for the primary and secondary beampaths are not shown in the figure, such ports are well known, and are easily implemented by one skilled in the art.

From the primary beampath 22, the x-ray beam enters the sample chamber and encounters the sample 50 located on the sample support 48. An XY translation stage 56 is connected to the sample support, and allows movement of the sample support in the two dimensions perpendicular to the beam direction. The translation stage, if desired, may also be movable parallel to the beam direction (i.e., may be an XYZ translation stage). The translation stage may be motorized, and may be operated manually or automatically. Typically, a stage such as this will have a position accuracy and repeatability in the micron or sub-micron range. The sample 50 itself may be supported on a frame, a foil or a nylon net, which is part of the sample support. The sample may also be fixed on the support mechanically or glued on a loading cartridge. In general, it is desirable to maintain the sample position on the XY stage while minimizing any x-ray attenuation caused by the support materials.

Also shown in FIG. 3 is an accessory port 58 to the sample chamber. The accessory port 58 may be one of a plurality of ports used to provide access or to accommodate measurement devices or sample environment control devices. For example, the accessory port 58 shown in FIG. 3 may be used for a two-dimensional detector that would allow the system to measure wide angle x-ray scattering (WAXS) as well as the small angle scattering simultaneously. In addition, it would also be possible to add an energy dispersive x-ray spectroscopy (EDXS) device for chemical element analysis.

Figure 4:
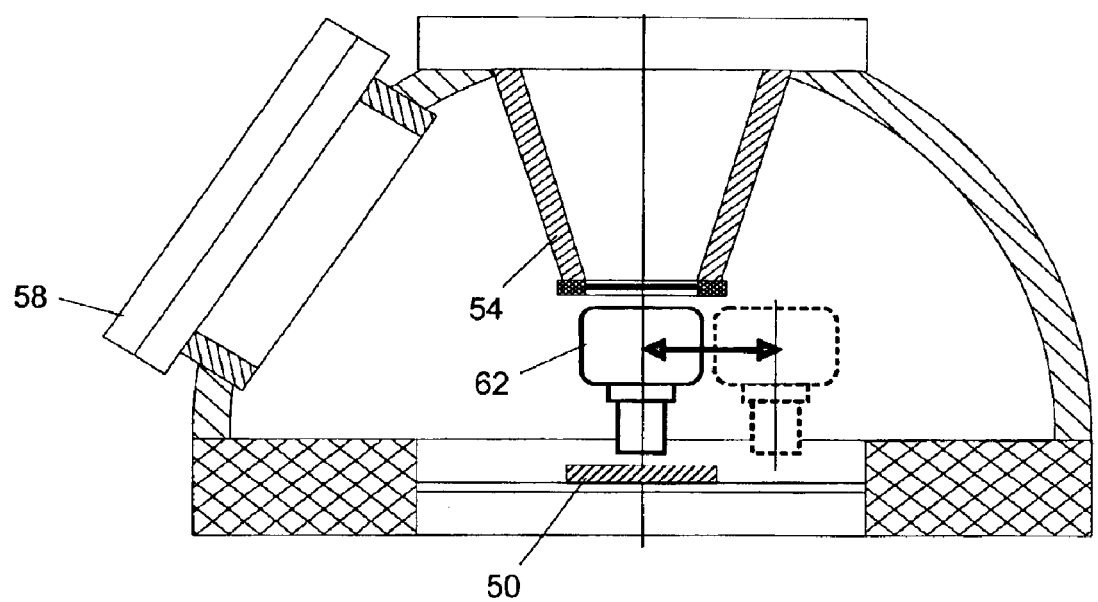
FIG. 4 is s schematic view of the interior of the sample chamber of the system of FIGS. 1A and 1B in which a movable video camera is used in place of an optical microscope.

Also connected to the sample chamber shown in FIG. 3 is optical microscope 60. The microscope may be used to observe the sample while it is located on the sample support. The microscope 60 is particularly useful for positioning of the sample prior to the x-ray scattering analysis. It allows a user to precisely align the sample so as to ensure that the appropriate section of the sample is being examined. Alternatively, a video microscope may be used that images the sample for either viewing by a user or input to an automatic positioning system. An example of such a video microscope is shown in FIG. 4. In this example, the video camera 62 (which may be magnifying) is movable between two positions, a "camera-on" position and a "camera-off" position. The video camera may be mounted on a track and may be movable either manually or automatically. For example, a small motor may be used to move the camera between the two positions. In the camera-on position, the camera is located directly above the sample, allowing a good view of the sample that does not suffer from the camera axis being at an angle relative to the x-ray beam axis. However, since the secondary beampath is obviously obscured by the camera in the camera-on position, it is moved to the camera-off position before scattering analysis commences. In FIG. 4, the solid line location of the camera indicates the camera-on position, while the dashed lines indicate the position of the camera in the camera-off position. It may be desirable to use the video image in conjunction with an automated sample positioning system that uses sample position information collected by the camera to adjust the XY translation stage to achieve a particular desired sample position.

The components of the secondary beampath are limited, and are best viewed in FIGS. 1A and 1B. The small-angle scattered x-ray energy 18 from the sample travels through the secondary beampath 25. The scattered energy is then incident on two-dimensional detector 12. Also located in the secondary beampath is beamstop 20. Since a portion of the initial x-ray beam passes through the sample without being scattered, it is desirable to inhibit it or attenuate it before it reaches the detector. The beamstop 20 may completely block the x-ray beam, or it may attenuate it to an acceptable degree. The attenuation may be by virtue of blocking all but a small portion of the x-ray beam, or by reducing the intensity of the beam overall. The advantage of this type of beamstop is that it allows the diffraction pattern and a transmission coefficient of the beam to be measured simultaneously at the detector 12.

The detector 12 may be a high sensitivity, low noise and high resolution two-dimensional detector such as a multiwire proportional counter (MWPC), which is known in the art. One example detector has a large imaging area (e.g., 11.5 cm diameter) for x-ray detection, and is sensitive to x-ray energy in a given wavelength range, such as the 3–15 KeV energy range. This example detector is a true photon-counting device, with an absolute detection efficiency of eighty percent. It can collect data frames of 1024×1024 (or 512×512) pixels with a pixel size of 100 $\mu$m (200 $\mu$m for 512×512 frames). Of course, the use of other detectors is also possible, and is well within the ken of one skilled in the art.

While the invention has been shown and described with reference to a preferred embodiment thereof, those skilled in the art will recognize that various changes in form and detail may be made herein without departing from the spirit and scope of the invention as defined by the appended claims.

What is claimed is:

1. A small angle x-ray scattering apparatus for providing small angle x-ray scattering analysis of a sample, the apparatus comprising:
   an x-ray source that outputs an x-ray beam in a vertical direction;
   a sample support that supports the sample and maintains it in a position that intersects the x-ray beam such that x-ray energy is scattered from the sample along angles close to said vertical direction;
   a sample chamber that surrounds the sample support;
   a primary beampath enclosure through which the x-ray beam from the x-ray source travels, an environment of the primary beampath enclosure being isolated from an environment within the sample chamber;
   a secondary beampath enclosure through which the x-ray energy scattered from the sample travels, an environment of the secondary beampath enclosure being isolated from the environment within the sample chamber;
   a beamstop that at least partially attenuates a central portion of the x-ray beam that passes through the sample unscattered; and
   an x-ray detector that receives and detects the x-ray energy scattered from the sample, the detector being positioned to detect x-ray energy that is scattered along angles of less than five degrees relative to said vertical direction.

2. An apparatus according to claim 1 further comprising an x-ray beam collimator that receives the x-ray beam from the x-ray source and collimates the x-ray beam before it reaches the sample.

3. An apparatus according to claim 1 further comprising a translation stage that is connected to the sample support and that is movable in at least two perpendicular directions to allow positioning of the sample.

4. An apparatus according to claim 3 wherein the translation stage is motorized.

5. An apparatus according to claim 1 wherein the primary beampath enclosure is evacuated.

6. An apparatus according to claim 1 wherein the secondary beampath enclosure is evacuated.

7. An apparatus according to claim 1 wherein the sample chamber is isolated from an external environment.

8. An apparatus according to claim 1 further comprising a first diaphragm that provides a fluid seal between the primary beampath enclosure and the sample chamber and a second diaphragm that provides a fluid seal between the sample chamber and the secondary beampath enclosure .

9. An apparatus according to claim 1 wherein the secondary beampath enclosure extends into the sample chamber.

10. An apparatus according to claim 1 further comprising an access port in the sample chamber that allows a user access to the sample.

11. An apparatus according to claim 1 further comprising a microscope positioned to view the sample.

12. An apparatus according to claim 11 wherein the microscope comprises a video camera.

13. An apparatus according to claim 12 wherein the microscope is movable between a first position that obstructs a path between the sample and the detector, and a second position in which it does not obstruct the path between the sample and the detector.

14. An apparatus according to claim 13 wherein the movement of the microscope is motorized.

15. An apparatus according to claim 1 wherein the x-ray beam travels in an upward direction.

16. An apparatus according to claim 1 wherein the x-ray beam travels in a downward direction.

17. An apparatus according to claim 1 further comprising beam conditioning optics in that receive the x-ray beam from the x-ray source and filter out wavelengths outside of a desired wavelength range.

18. A small angle x-ray scattering apparatus for providing small angle x-ray scattering analysis of a sample, the apparatus comprising:
   a sample chamber;
   a primary beampath enclosure located adjacent to the sample chamber and oriented in a vertical direction, an environment of the primary beampath enclosure being isolated from an environment within the sample chamber;
   an x-ray source that outputs an x-ray beam along said vertical direction through the primary beampath enclosure;
   beam conditioning optics that receive the x-ray beam from the x-ray source and filter out wavelengths outside of a desired wavelength range;
   a collimator that collimates the x-ray beam output from the x-ray source;
   a sample support located in the sample chamber that supports the sample and maintains it such that x-ray energy from the collimator encounters the sample and is scattered from the sample at small angles relative to the vertical direction;
   a secondary beampath enclosure that is located to a side of the sample chamber opposite the primary beampath enclosure, and that receives the x-ray energy scattered from the sample an environment of the secondary beampath enclosure being isolated from an environment within the sample chamber;
   a beamstop that at least partially attenuates a central portion of the x-ray beam that passes through the sample unscattered; and
   an x-ray detector located in the secondary beampath enclosure that receives and detects the x-ray energy scattered from the sample, the detector being positioned to detect x-ray energy that is scattered along angles of less than five degrees relative to the vertical direction.

19. A method for providing small angle x-ray scattering analysis of a sample, the method comprising:
   generating an x-ray beam with an x-ray source that outputs the beam in a vertical direction;
   locating the sample on a sample support that resides in a sample chamber and that supports the sample and maintains it in a position that intersects the x-ray beam such that x-ray energy is scattered from the sample along angles close to said vertical direction;
   providing a primary beampath enclosure through which the x-ray beam from the x-ray source travels, an environment of the primary beampath enclosure being isolated from an environment within the sample chamber;
   providing a secondary beampath enclosure through which the x-ray energy scattered from the sample travels, an environment of the secondary beampath enclosure being isolated from the environment within the sample chamber;
   at least partially attenuating a central portion of the x-ray beam that passes through the sample unscattered with a beamstop; and
   detecting the scattered x-ray energy with an x-ray detector that receives and detects the x-ray energy scattered from the sample, the detector being positioned to detect x-ray energy that is scattered along angles of less than five degrees relative to said vertical direction.

20. A method according to claim 19 further comprising collimating the x-ray beam before it reaches the sample with an x-ray beam collimator.

21. A method according to claim 19 further comprising connecting the sample support to a translation stage that is movable in at least two perpendicular directions to allow positioning of the sample.

22. A method according to claim 21 wherein the translation stage is motorized.

23. A method according to claim 19 wherein the primary beampath enclosure is evacuated.

24. A method according to claim 19 wherein the secondary beampath enclosure is evacuated.

25. A method according to claim 19, wherein the sample chamber is isolated from an external environment.

26. A method according to claim 19 further comprising sealing the primary beampath enclosure from the sample chamber with a first diaphragm that provides a fluid seal and sealing the sample chamber from the secondary beampath enclosure with a second diaphragm that provides a fluid seal.

27. A method according to claim 19 wherein the secondary beampath enclosure extends into the sample chamber.

28. A method according to claim 19 further comprising providing an access port in the sample chamber that allows a user access to the sample.

29. A method according to claim 19 further comprising viewing the sample with a microscope.

30. A method according to claim 29 wherein the microscope comprises a video camera.

31. A method according to claim 30 wherein the microscope is movable between a first position that obstructs a path between the sample and the detector, and a second position in which it does not obstruct the path between the sample and the detector.

32. A method according to claim 31 wherein the movement of the microscope is motorized.

33. A method according to claim 19 wherein the x-ray beam travels in an upward direction.

34. A method according to claim 19 wherein the x-ray beam travels in a downward direction.

35. A method according to claim 19 further comprising filtering the x-ray beam with beam conditioning optics to remove wavelengths outside of a desired wavelength range.

* * * * *